(12) United States Patent
Scaringe et al.

(10) Patent No.: US 6,514,765 B1
(45) Date of Patent: Feb. 4, 2003

(54) ACID TEST KIT AND METHOD OF USE

(75) Inventors: Robert P. Scaringe, Rockledge, FL (US); Nidal A. Samad, Palm Bay, FL (US)

(73) Assignee: Mainstream Engineering Corporation, Rockledge, FL (US)

( * ) Notice: Subject to any disclaimer, the term of this patent is extended or adjusted under 35 U.S.C. 154(b) by 0 days.

(21) Appl. No.: 08/423,211

(22) Filed: Apr. 17, 1995

(51) Int. Cl.⁷ ................................. G01N 33/18
(52) U.S. Cl. ................ 436/39; 436/164; 436/169; 436/177; 422/58; 422/61; 422/86; 422/104
(58) Field of Search .............. 422/61, 83, 86, 422/58, 87–88, 101, 102, 104; 436/100, 163, 164, 167, 169, 177, 38, 39

(56) References Cited

U.S. PATENT DOCUMENTS

| | | | |
|---|---|---|---|
| 3,084,658 A | | 4/1963 | Schell |
| 4,789,638 A | * | 12/1988 | Kramer et al. ............. 422/83 |
| 4,923,806 A | * | 5/1990 | Klodowski ................. 422/86 |
| 5,071,768 A | | 12/1991 | Klodowski |
| 5,127,433 A | | 7/1992 | Argyle et al. |
| 5,171,536 A | * | 12/1992 | Evers ..................... 422/86 |
| 5,363,661 A | * | 11/1994 | Condit et al. ............. 422/83 |
| 5,377,496 A | | 1/1995 | Otto et al. |

* cited by examiner

*Primary Examiner*—Lyle A. Alexander
(74) *Attorney, Agent, or Firm*—Crowell & Moring LLP

(57) ABSTRACT

An acid test kit uses an indicator paper in a transparent tube which is easily and temporarily inserted in a Schrader-valve at a compressor suction inlet of a refrigeration system. The simplicity, yet sufficient accuracy, of the kit permits several different ways of holding the paper in the tube through a friction fit. One way is to sandwich the paper between a tapered holder which is folded to provide a nose for actuating the Schrader valve. Another way is to provide the paper on or over a cylindrical member. A method for using the test kit including allowing vapor refrigerant from the system to pass through the tube to the atmosphere.

28 Claims, 4 Drawing Sheets

ACID TEST KIT AND METHOD OF USE

BACKGROUND AND SUMMARY OF THE INVENTION

The present invention relates to an acid test kit and, more particularly, to an acid test kit used in vapor compression refrigerators and the like in which an indicator paper is held in a transparent tube-like fixture to monitor the acid level in the system simply, quickly and inexpensively.

Vapor compression refrigerators, heat pumps, and air conditioners must always be concerned with the presence of acids in the refrigerant which can severely shorten the life of both the compressor and the refrigerant. These acids can be formed by chemical reactions with components and/or materials of construction, lubricating oils, and/or impurities. The instability of the refrigeration, and thus the formation of acids, is accelerated by elevated temperatures which result from improper operation, such as a failed condenser fan, or clogged air flow path.

Checking the refrigerant and/or oil acid is a common maintenance procedure because acidic refrigerant can be cleaned up before permanent damage to the hardware and refrigerant occur. Acidic refrigerant will also result in hermetic compressor motor burn-out because the acid will degrade the motor winding's electrical insulation. Moreover, the presence of acid indicates the existence of other decomposition products, such as non-condensable gases, which result in elevated pressures and increased compressor pressure ratios leading to reduced efficiency and overloaded compressor operation.

To avoid the above-mentioned problems, refrigeration systems are tested for acid content. Typically, the oil would be tested for acid, because the highest concentration of acid is found in the oil of a non-operating system (shut down). It is, however, much easier to test the refrigerant for acid instead of testing the oil for acid, since the refrigerant is pressurized and existing service valves provide an easy way of sampling the refrigerant. Testing of the refrigerant vapor, rather than the refrigerant liquid, of the system is much more convenient because testing the liquid refrigerant results in a much greater refrigerant loss and the exiting liquid will cause frostbite if not properly handled.

Visual sensors or indicators for use in detecting the corrosive state of a fluid in a heat exchanger system are known as seen, for example, in U.S. Pat. No. 5,127,433. A permanently installed sensor has a sight glass or window through which corrosiveness is determined by viewing a flap or ball displaying a color indicating either the need to change the fluid or to add corrosion inhibitors. Alternatively, corrosiveness can be indicated by a ruptured or broken diaphragm located between the sight glass and the fluid. This form of sensor is limited to applications such as automobile cooling systems where the sensor is provided in the overflow conduit or in the hot fluid conduit upstream of the radiator.

Humidity and corrosion indicators for packaged goods in which thin cobaltous chloride film is used as the sensing element are described in U.S. Pat. No. 3,084,658. An elastomeric grommet sealed by a transparent disk is inserted into an opening in a package wall. A disk impregnated with the cobaltous chloride is secured beneath a window and can be replaced.

With respect to closed refrigeration systems, other types of indicator systems are known for testing the presence and concentration of contaminants in a refrigerant. For example, U.S. Pat. Nos. 4,923,806 and 5,071,768 show apparatuses for testing liquid or vapor contaminants in a closed system regardless of whether the apparatus is operating or not. A disposable testing tube made of transparent material is used at the end of a compressor discharge line or elsewhere in the system. One section of the tube is provided with water removal and moisture indicating chemicals, such as cobaltous chloride and another section is provided with acid indicating chemicals such as a solution of bromophenol blue, ethanol and glycerol. This construction is relatively complicated and requires a separate, specially configured flow restrictor in addition to a tube holder, and an expensive testing tube in which the multiple contaminant testing chemicals and filter screens are permanently located.

Likewise, U.S. Pat. No. 5,377,496 shows an acid contamination indicator for closed loop vapor compression refrigeration systems in which the indicator is permanently or removably installed in the bypass line around the system compressor where the refrigerant is always in the gaseous phase. A casing has a visual indicator bed of bromophenol blue as the acid indicating medium which is contacted by the refrigerant after flowing through a filter and a flow restrictor orifice. Porous retainer disks are held against the bed by springs. Moreover, the indicator, which changes color when exposed to acids or bases, are solid, and thus they must be exposed to the test stream in some fashion. Accordingly, this solid indicator must be mixed with an inert substance to provide some porosity, contact surface area and increased volume and then packaged in a clear tube. The vapor refrigerant is then passed through the porous mixture arranged in a bypass loop between the suction and discharge ends of a compressor or in the main refrigerant flow path between the compressor discharge and a heat exchanger to observe a color change. Again, we have recognized that this is an unduly complicated construction which requires a substantial outlay for installation.

Another type of contaminant detector is marketed by Refrigeration Technologies of Fullerton, California under the trademark "CHECKMATE". A specific volume of gas passes through a detection tube at a predetermined termination pressure. However, an expensive sealed Pyrex detection tube containing a color-changing chemical and whose ends are pierced when fully assembled can only be used once even when the test is negative, and thus this approach entails considerable expense regardless of its technical merits.

In a vapor-compression system, refrigerant flows from the condenser to the expansion valve, where it flashes into a two-phase mixture and then enters the evaporator. Superheated refrigerant vapor, with some entrained oil, leaves the evaporator and is compressed in the compressor, before being condensed in the condenser to complete the cycle. When in chemical equilibrium, the majority of the acid in the system is contained in the oil, but acid is also present in the liquid and vapor refrigerant. The presence of water in the system, which is a very real possibility, causes an even greater concentration of the acid in the liquid rather than in the vapor. To further complicate the problem, the relative liquid and vapor acid concentrations are a function of the system's liquid and vapor volume and therefore are system dependent. These factors all render the measurement of acid level in the refrigerant's equilibrium vapor phase an uncertain indication of acid level in the compressor oil.

Although the acid content in the refrigerant vapor can not be exactly correlated to the compressor oil acid content, it is, however, accurate enough to indicate the relative status of the oil in the system. It is clear that when acid is detected in the vapor, the acid level in the oil is significantly higher.

Independent of the system, it can be generally stated that a refrigerant vapor acid level about 1–2 parts per million (ppm) in the refrigerant vapor clearly means the oil acid content is high, and the system should be cleaned up to reduce the acid level. Furthermore, a refrigerant vapor acid level of 10 ppm, clearly indicates the compressor's oil acid level is well beyond safe operating levels and the system will fail shortly if the refrigerant and acid is not changed or cleaned.

We have discovered that a pH paper can provide a simple fast and extremely inexpensive way to test for acidity in a refrigeration system. It allows for testing with the system on or off, and in other applications as well. In addition, it does not have to be installed in a line but can be temporarily connected with, for example, a Schrader-valve to permit venting of a small amount of gaseous refrigerant to the atmosphere. This is a surprising discovery because a pH paper is typically used to measure the concentration of hydronium ions in an aqueous solution. However, an aqueous solution is not present in a refrigerant system. Table 5–30 of *Lanqe's Handbook of Chemistry* (13th Edition) lists several chemical compounds for colorimetric pH indicators as follows:

| Indicator | Chemical Name | pH Range | $pK_a$ | $\lambda_{max}$, nm | Color Change |
|---|---|---|---|---|---|
| Cresol red (acid range) | o-Cresolsulfonephthalein | 0.2 to 1.8 | | | R–Y |
| Cresol purple (acid range) | m-Cresolsulfonephthalein | 1.2 to 2.8 | 1.51 | 533, . . . | R–Y |
| Thymol blue (acid range) | Thymolsulfonephthalein | 1.2 to 2.8 | 1.65 | 544, 430 | R–Y |
| Tropeolin 00 | Diphenylamino-p-benzene sodium sulfonate | 1.3 to 3.2 | 2.0 | 627, . . . | R–Y |
| 2,6-Dinitrophenol | 2,6-Dinitrophenol | 2.4 to 4.0 | 3.69 | | C–Y |
| 2,4-Dinitrophenol | 2,4-Dinitrophenol | 2.5 to 4.3 | 3.90 | | C–Y |
| Methyl yellow | Dimethylaminoazobenzene | 2.9 to 4.0 | 3.3 | 508, . . . | R–Y |
| Methyl orange | Dimethylaminoazobenzene sodium sulfonate | 3.1 to 4.4 | 3.40 | 622, 464 | R–O |
| Bromophenol blue | Tetrabromophenolsulfonephthalein | 3.0 to 4.6 | 3.85 | 436, 592 | Y–BV |
| Bromocresol green | Tetrabromo-m-cresol-sulfonephthalein | 4.0 to 5.8 | 4.58 | 444, 617 | Y–B |
| Methyl red | o-Carboxybenzeneazo-dimethylaniline | 4.4 to 6.2 | 4.95 | 530, 427 | R–Y |
| Chlorophenol red | Dichlorophenolsulfonephthalein | 5.4 to 6.8 | 6.0 | . . . , 573 | Y–R |
| Bromocresol purple | Dibromo-o-cresolsulfonephthalein | 5.2 to 6.8 | 6.3 | 433, 591 | Y–P |
| Bromophenol red | Dibromophenolsulfonephthalein | 5.2 to 6.8 | | . . . , 574 | Y–R |
| p-Nitrophenol | p-Nitrophenol | 5.3 to 7.6 | 7.15 | 320, 405 | C–Y |
| Bromothymol blue | Dibromothymolaulfonephthalein | 6.2 to 7.6 | 7.1 | 433, 517 | Y–B |
| Neutral red | Aminodimethylaminotoluphenazonlum chloride | 6.8 to 8.0 | 7.4 | | R–Y |
| Phenol red | Phenolsulfonephthalein | 5.4 to 8.0 | 7.8 | 433, 558 | Y–R |
| m-Nitrophenol | m-Nitrophenol | 5.4 to 8.8 | 8.3 | . . . , 570 | C–Y |
| Cresol red | o-Cresolsulfonephthalein | 7.2 to 8.8 | 8.2 | 434, 572 | Y–R |
| m-Cresol purple | m-Cresolsulfonephthalein | 7.5 to 9.2 | 8.32 | . . . , 580 | Y–P |
| Thymol blue | Thymolsulfonephthalein | 8.0 to 9.6 | 8.8 | 430, 596 | Y–B |
| Phenolphthalein | Phenolphthalein | 8.0 to 10.0 | 9.4 | . . . , 553 | C–R |
| α-Naphtholbenzein | α-Naphtholbenzein | 9.0 to 11.0 | | | Y–B |
| Thymolphthalein | Thymolphthalein | 9.4 to 10.6 | 10.0 | . . . , 598 | C–B |
| Allzarin Yellow R | 5-(p-Nitrophenylazo)-salicylic acid, Na salt | 10.0 to 12.0 | 11.16 | | Y–V |
| Tropeolin 0 | p-Sulfobenzeneazo-resorcinol | 11.0 to 13.0 | | | Y–O Br |
| Nitramine | 2,4,6-Trinitrophenyl-methylnitroamine | 10.8 to 13.0 | | | C–O Br |

These compounds change color depending on the form they take (for example, yellow when acidic and blue when basic). A pH paper is a filter paper totally impregnated with one or more of these indicator compounds, generally an organic compound, that is a weak acid with a certain pKa (pKa is defined as the negative log of the dissociation equilibrium constant). The pKa value determines the range of the indicator.

Specifically for our invention, we currently contemplate use of a pH paper manufactured by Micro Essential Laboratory, Brooklyn, N.Y. with a pH range of 1–6. This pH paper is impregnated with meta-cresol purple (trade name)

also known as meta-cresolsulfonephthalein (chemical name). The structure of this chemical is given below:

This indicator, meta-cresol purple, is red in acidic form and yellow in the basic form.

Our invention does not measure pH because the systems and the like with which the acid test kit is intended to be used do not contain an aqueous solution. We utilize pH paper because of the surprising discovery that it has an indicator which will react with the inorganic acid vapor present in the refrigeration system. Furthermore, filter paper impregnated with indicator solution is a commercially available product, namely pH paper, thus lowering the cost even more.

Thus, the present invention takes advantage of the low cost and ready availability of pH paper. If the indicator is in an acidic environment, the indicator will react with the acid and produce a red color. If the acid concentration is not enough to turn the indicator completely red, however, an intermediate color, between red and yellow (that is some shade of orange) will be observed. Therefore, the intensity of the color is concentration dependent. On the pH paper, a certain amount of the indicator is impregnated, and as the acid reacts with the indicator, the indicator's color changes. When most of the indicator has reacted, a red color will be observed. Therefore, the intensity of the color change depends on what percentage of the indicator has been transformed (reacted) to the acidic form.

We have also found that in a refrigeration system the refrigerant vapor acid test should be performed from the suction (vapor) service port. If both a compressor suction-side and compressor discharge-side vapor connection is available, we have further recognized that the lower-pressure suction side should be used and the system should be operating in order to minimize the amount of oil discharged with the refrigerant vapor and will also serve to provide a more acidic sample. When the vapor-compression compression system is operating, the liquid refrigerant with some dissolved oil is vaporized in the evaporator, resulting in an acid vapor refrigerant flow with entrained liquid oil droplets.

The acid level of the vapor stream during operation is is not at equilibrium but instead is essentially the same as the acid level of the liquid that the refrigerant was flashed or evaporated from. Because the vapor is safer and much easier to sample, the sampling of the vapor phase during system operation is a much easier, safer, faster and better approach, as long as the system is operating, and will provide essentially the same accuracy as sampling of the liquid. In other words, although the equilibrium concentration of the acid in the vapor is lower than the acid concentration in the liquid refrigerant when the system is off (and would, therefore, provide lower and inaccurate pH readings), when the system is running (i.e., compressor operating, refrigerant flowing), the liquid refrigerant with acid and dissolved oil is flashed (evaporated) into superheated refrigerant vapor and entrained oil, and the acid is carried along with this vapor so that the acid level of this vapor is essentially the same as the acid level in the liquid refrigerant. Nevertheless, the acid test kit can be used in a system which has been shut off or in relation to a tank of recovered refrigerant. For those non-operational systems which need to be repaired, the oil can be tested directly (or simply changed) while the system is being repaired and thus does require an acid indicator which is safe and easy to use.

It is, therefore, an object of the present invention to provide an accurate, yet simple and inexpensive, acid test device which can sample the refrigerant's acid level, by sampling the refrigerant vapor, from existing system service valves, or from a refrigerant recovery tank, to provide an indication of the condition of the refrigerant and therefore the condition of the system.

In order to determine the pH of the vapor sample, it is necessary for a known amount of refrigerant be used in the test. We have further developed a simple method of determining this known amount of refrigerant. All systems typically have service valves with valve core depressors (often referred to as Schrader-valves). These valves, like automobile tire-valves, are opened when a valve core is depressed, usually by the device being attached to the valve. For refrigeration systems, these types of service valves with valve core depressors are used in several standard sizes, with ¼" being the most common and ⅜", ½", and ⅝" also used. For a given valve size, these service valves have a known flow cross-section. In order to determine the pH of the vapor sample, it is necessary to use a known amount of refrigerant. The present invention also uses these service valves as the flow metering device. In addition, for a given refrigerant, the system pressures are known, from the saturation pressure temperature correlation for the refrigerant. Therefore the combination of the known cross-section orifice area (service valve cross-sectional flow area) and known pressure can be used to calibrate refrigerant flow and therefore to calibrate acid level with the time necessary to react the indicator, that is to obtain a specific color change on the indicator.

The present invention advantageously uses a readily available, inexpensive indicator paper held in a transparent tube-like fixture to monitor the acid level. Indicator chemistry reaction is essentially a function of acid level and exposure time in an essentially linear fashion. That is, half the acid level exposed for twice the time will result in the same indicator reaction. Therefore, as discussed above, the effect of refrigerant flow must be considered in determining acid level. The present invention uses a standard refrigeration service valve with valve-core depressor (Schrader-valve), an industry-standard service valve, which is already present in essentially all refrigeration systems, as the natural throttling or metering device on the system. The system pressure depends only on the system refrigerant, thus advantageously allowing performance tables to be developed for each refrigerant.

BRIEF DESCRIPTION OF THE DRAWINGS

These and other objects, features and advantages of the present invention will become more readily apparent from the following detailed description thereof when taken in conjunction with the accompanying drawings wherein.

DETAILED DESCRIPTION OF THE DRAWINGS

Figure 1:
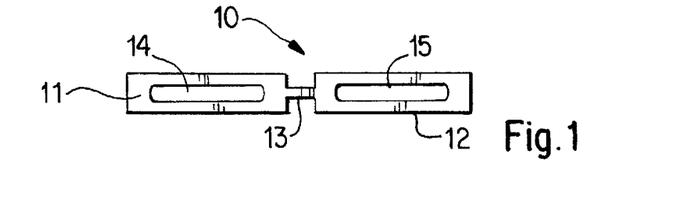
FIG. 1 is a side view of a slightly tapered indicator paper holder of the present invention in an unfolded position.
Figure 2:
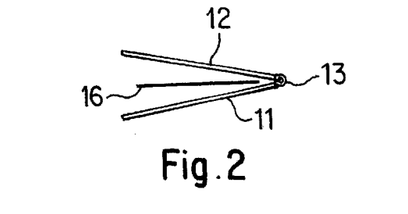
FIG. 2 is a plan view of the holder of FIG. 1 but in a partially folded condition with a piece of indicator paper in between legs of the holder.
Figure 3:
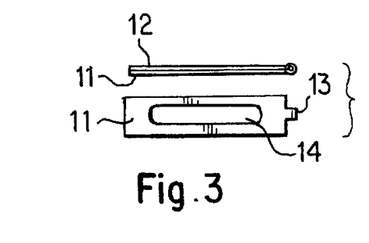
FIG. 3 shows a side view of the holder of FIGS. 1 and 2 and a top view thereof in the fully folded position.

Referring now to FIG. 1, the acid indicator for a test kit is indicated generally by reference numeral 10 and consists of a holder having two slightly tapering panel portions 11, 12 joined by a connecting strip 13 whose additional function is described below. Each of the panel portions 11, 12 has an elongated aperture 14, 15, respectively, to expose a test paper to refrigerant vapor. A standard piece of sheet-like pH-type acid test paper 16 is pinched or sandwiched between the panel portions 11, 12 which are folded together as seen in FIG. 2 into the final folded position of FIG. 3 with the connecting stop 13 forming a projecting nose or dimple.

Figures 4, 5:
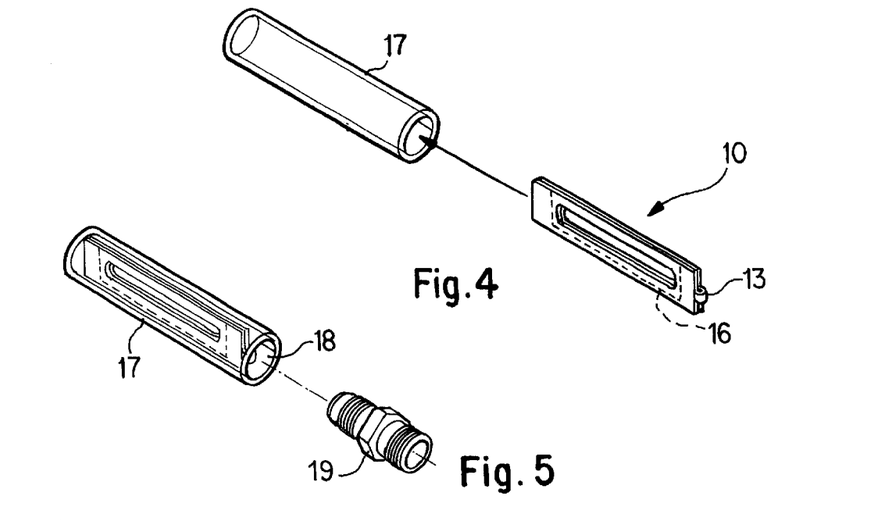
FIG. 4 is a perspective view showing insertion of the fully folded holder of FIG. 3 in an external tube.
FIG. 5 is a perspective view of the assembled holder and external transparent tube constituting a test kit with indicator paper showing attachment of a service valve.
Figure 6:
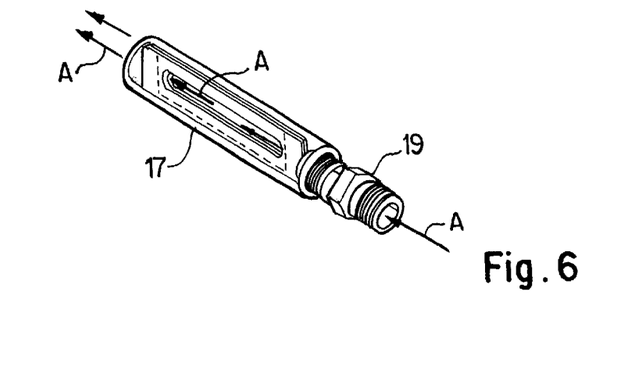
FIG. 6 is a perspective view of the assembled external tube and service valve of FIG. 5.

The acid indicator insert 10 fitted with the pH test paper 16 is then inserted into a clear tube 17 as seen in FIG. 4. The small raised dimple or nose formed by the folded connecting strip 13 is arranged at the tube inlet 18 as seen in FIG. 5 and is advantageously used to depress a valve core of the system's vapor-service-valve 19 which allows refrigerant vapor to flow through the test kit 10 in the manner shown by the arrows A in FIG. 6 to contact the paper 16 exposed through the apertures 14, 15. The external clear tube 17 directs the refrigerant vapor past the indicator paper 16, and the refrigerant is then exhausted into ambient air. The total time for the test is less than 15 seconds. Refrigerant vapor, not liquid, is tested by holding the test kit 10 against the system's vapor service valve 19, typically the valve on compressor suction-side and only when the compressor (not shown) is operating.

In one embodiment of the present invention, the folded insert 10 is fabricated from a plastic material colored to the same color as the un-reacted indicator paper 16 held therewithin. Using the above-mentioned pH paper having a range of pH of 1.2 to 2.8, for example, the unreacted paper is yellow and after reaction the paper color is orange or red. The test kit operator holds the test kit against the refrigeration system's vapor service Schrader-valve for a five second count. If the indicator paper remains yellow by comparing it with the surrounding yellow plastic panel portions 11, 12, then the acid level is deemed to be below 1–2 ppm, and the refrigerant and oil in the system are considered acceptably uncontaminated.

If the indicator paper turns orange within the five second count, however, acid is deemed present in the refrigerant vapor, and therefore also in the oil, at an unacceptable level above safe operating conditions. The refrigerant should then be cleaned or replaced. If recovered refrigerant is being tested, the refrigerant should be recycled to an acceptable acid level before using in a system. If the indicator paper 16 turns red, there is a very high acid level in the refrigerant vapor and the oil. Both the oil and refrigerant should be changed immediately, otherwise system failure is imminent, and this refrigerant should not be recycled. Finally, if the indicator paper 16 remains yellow, the acid test kit can be exposed to refrigerant for another five seconds while the system is running. If the indicator paper 16 still remains yellow, the acid content is very low, below 0.5–1.0 PPM. If, however, the indicator turns orange or red, clean up procedures should still be instituted.

A more accurate, but also somewhat more expensive, alternative approach is to color the plastic indicator holder 10, for example, orange for the type of pH paper used in this embodiment. The test kit user then holds the indicator 10 in the clear tube 17 on the service valve 19 is and counts the number of seconds it takes for the paper indicator to turn the orange color of the surrounding plastic panel portions 11, 12. The time it takes to turn the indicator 10 to the specified color (that is the color of the plastic holder), is compared to a table for the particular refrigerant being tested to determine the acid content of the refrigerant. The test kit is configured so that if no color change occurs after fifteen seconds the test is stopped because essentially no acid is present.

Several other configurations of indicators can be used as shown in FIGS. 7 through 10, where parts similar in function to the parts in FIGS. 1–6 are designated by the same numerals but primed. There are also several other standard indicator solutions, such as bromophenol blue and meta-cresol purple, which can be used for acid testing. Ordinary pH paper, which is typically used only for acid tests in aqueous solutions, has been found to work very well in the present invention because the results are repeatable, accurate, and fast. Alternatively, any standard indicator solution can also be used directly on the test kit's insert 10 by configuring the panel portions 11, 12 of paper which is directly treated with indicator chemistry. A currently contemplated embodiment is that shown in FIGS. 1–6 and contemplates using commercially available pH paper sandwiched into the color-coded bracket 10 which is slipped into the clear, slightly elastic tube 17 which is sized to be deformed into an oval cross-section upon insertion of the slightly tapered paper holder 10 into the tube 17 to insure a tight friction fit.

Figures 7, 8:
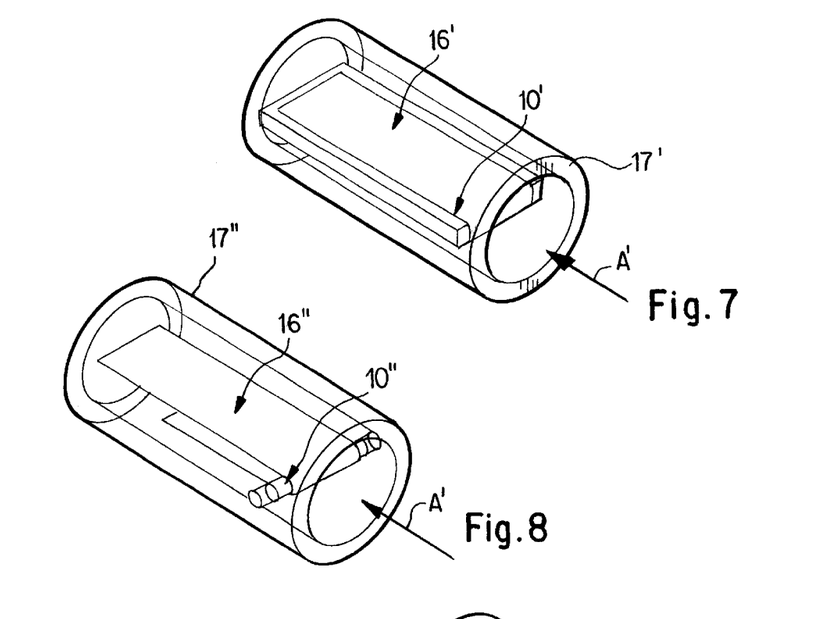
FIG. 7 is a side view similar to FIG. 5 but showing a second embodiment of indicator holder.
FIG. 8 is a view similar to FIG. 5 but showing a third embodiment of indicator holder.
Figures 9, 10:
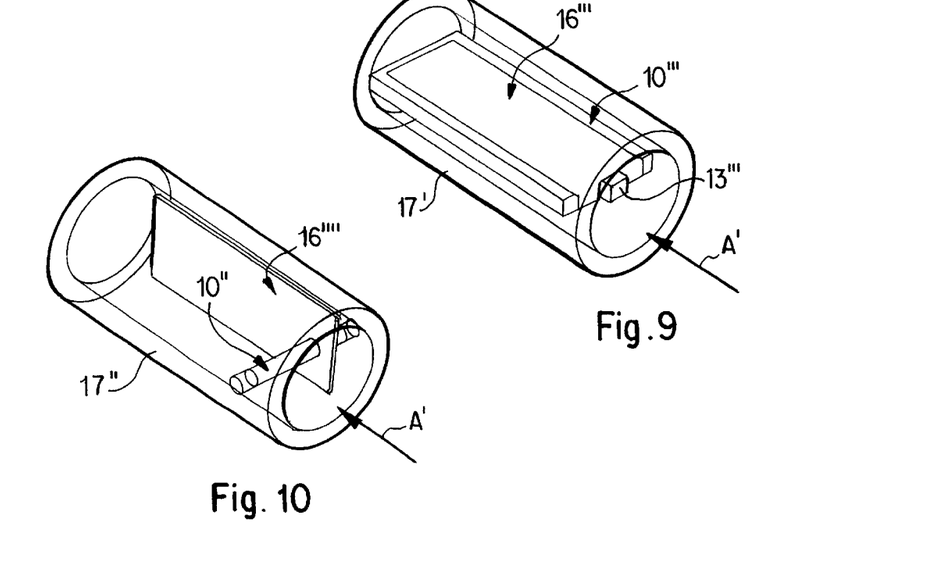
FIG. 9 is a view similar to FIG. 5 but showing a fourth embodiment of indicator holder.
FIG. 10 is a view similar to FIG. 5 but showing a fifth embodiment of indicator holder.

In the embodiment of FIG. 7, the holder 10' is a solid piece over which a piece of indicator paper 16' is laid before insertion into the tube 17'. In the embodiment of FIG. 8, the holder 10" is in the form of a cylindrical member installed in the clear tube 17" such that a piece of indicator paper 16" can be wrapped over the holder 10". The embodiment of FIG. 9 is similar to the embodiment of FIG. 7, except that the holder 10'" has a projecting nose 13'" similar in function to the nose or dimple used in the embodiment in FIGS. 1–6. The indicator paper 16'" has an opening through which the nose 13'" extends. The embodiment of FIG. 10 is similar to the embodiment of FIG. 8 except that the indicator paper 16'" has an aperture through which the cylindrical member 16'" is inserted before insertion into the clear tube 17".

The indicator paper holder 10 can, for example, be fabricated from flat colored plastic or metal which is folded into the frame holding the indicator paper as shown in FIGS.

1–6. This embodiment, which forms a rounded nose 13 has a wider surface for depressing the Schrader valve and allows use of a thinner material, such as 0.020". Because of the rounded nose 13, however, the frontal area which depresses the Schrader-valve is much thicker, e.g. approximately 0.090" depending upon the material used and its ductility. This insert can also be slightly tapered along its long sides, as seen in FIG. 1, to allow easier insertion into the clear somewhat elastic tube 17, the width of the insert 10 being, for example, about 0.050" wider that the diameter of the tubing 17 to insure a tight friction fit.

Figures 11A, 11B, 11C:
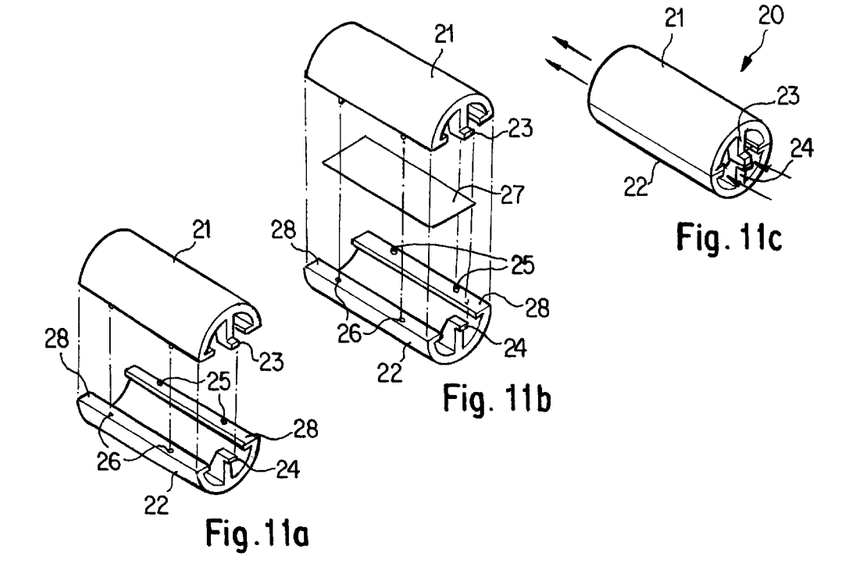
FIG. 11 consists of exploded views (a)–(e) showing another test kit embodiment in accordance with the present invention.
Figure 11D:
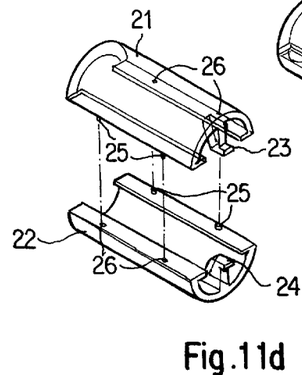
Figure 11E:
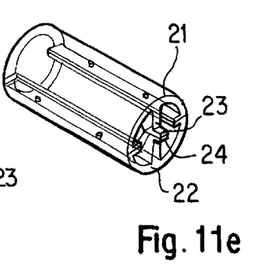
Figure 12A:
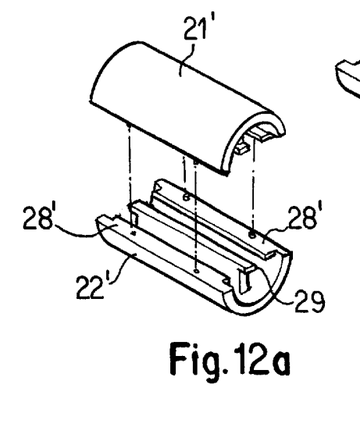
FIG. 12 consists of exploded views (a)–(e) showing yet another test kit embodiment in accordance with the present invention.
Figure 12B:
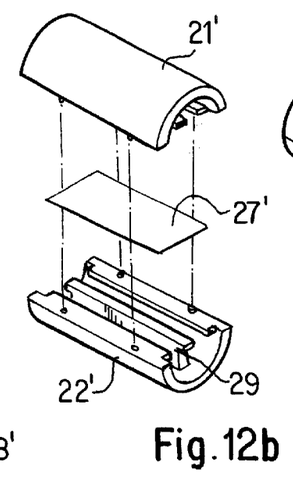
Figure 12C:
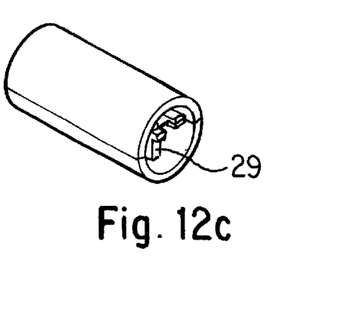
Figure 12D:
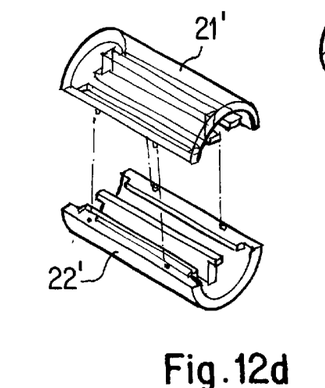
Figure 12E:
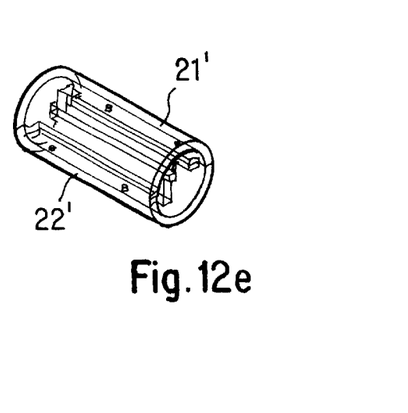

A currently preferred embodiment of the present invention as shown in FIG. 11, the test kit 20 is fabricated from two mating injection-molded and symmetrical parts 21, 22 molded from clear plastic material. Each half 21, 22 of the injected molded holder 20 has a raised dimple 23, 24 at the tube inlet which is used to depress the system's vapor-service-valve valve-core and allows refrigerant vapor to flow. On one side of both halves 21, 22 of the molded holder 20 are crush pins 25 which deform into mating holes 26 on the other half to lock the halves together as best seen in the views (d) and (e) in FIG. 11. No glue or adhesive is used to avoid adversely affecting the pH paper 27. A shelf or frame 28 is also molded into both halves 21, 22 to pinch and hold the indicator paper 27 in place.

To further simply the fabrication of the molded holder, a third embodiment of the present invention as seen in FIG. 12 is provided. To simplify fabrication, the raised dimple sections 23, 24 of FIG. 11 has been replaced by a complete center shelf 29 which also serves as an additional pinch point for the indicator paper. All other features of this embodiment remain the same as in FIG. 11 and therefore are designated by the same numerals but primed.

After fabrication, the acid test kit in each of the above-described embodiments is packaged in an airtight plastic bag to avoid contamination prior to use.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A test kit, comprising a hollow transparent member open at upstream and downstream ends thereof, and an acid indicator assembly having a holder fixture and a sheet-like substrate operatively held by the holder fixture so as to define a free cross section disposed along a flow of gaseous refrigerant through the member removably and securely held within the member, wherein the upstream end of the member is configured to be held temporarily against a service valve at one of a compressor suction side inlet of a refrigeration system and a recovered refrigerant vessel for permitting the flow of gaseous refrigerant through the member and over an outer surface of the substrate into the atmosphere.

2. The test kit according to claim 1, wherein the acid indicator assembly is a cylindrical piece extending transversely of the transparent member, and pH-type acid paper is arranged to extend around the piece in a downstream direction of the transparent member.

3. The test kit according to claim 1, wherein the acid indicator assembly is a cylindrical piece extending transversely of the transparent member, and a pH-type acid paper with an aperture through which the piece is arranged to extend a downstream direction of the transparent member.

4. The test kit according to claim 1, wherein the substrate is planar with outer facing surfaces of the planar substrate being substantially parallel to the flow of the gaseous refrigerant.

5. The test kit according to claim 1, wherein the holder fixture is one of integrated with the hollow transparent member and a separate piece.

6. The test kit according to claim 1, wherein the holder fixture includes a flat rigid holder and pH-type acid paper extending along one side of the holder over an upstream face of the holder and along another side of the holder.

7. The test kit according to claim 6, wherein the holder has a dimple at the upstream face, and the paper has an aperture through which the dimple extends to open the service valve constituted by a Schrader-valve.

8. The test kit according to claim 1, wherein the holder fixture has two panels arranged to be folded together with a pH-type acid indicator paper therebetween, said fixture being sized to provide a tight friction fit with the transparent member.

9. The test kit according to claim 8, wherein the panels have a color matching a color of the paper in an unreacted state.

10. The test kit according to claim 8, wherein the panels have a color matching a color of the paper in an reacted state.

11. The test kit according to claim 8, wherein the fixture defines a dimple between the panels at the upstream side of the member, the dimple being configured to open the service valve constituted by a Schrader-valve.

12. The test kit according to claim 11, wherein the transparent member is a cylindrically-shaped tube.

13. The test kit according to claim 8, wherein each of the panels has an aperture to expose the indicator paper held therebetween to the gaseous refrigerant flow from the service valve.

14. The test kit according to claim 13, wherein the dimple constitutes a bridging portion joining the panels.

15. A test kit, comprising a transparent member consisting of two portions arranged to be joined together and open at upstream and downstream ends thereof, each of the portions having a raised dimple segment at the upstream end and a shelf at each joint face for holding securely therebetween a pH-type acid paper having a sheet-like substrate along a flow of gaseous refrigerant through the member such that the gaseous refrigerant flows over an outer surface of the substrate, wherein the raised dimple segments, in an assembled state, constitute a dimple configured to open a Schrader-valve when the kit is temporarily held against the valve for permitting the flow of gaseous refrigerant therethrough to the atmosphere.

16. A test kit, comprising a transparent member consisting of two portions arranged to be joined together and open at upstream and downstream ends thereof, each of the portions having a raised dimple segment extending from the upstream end to the downstream end to define a shelf and a shelf at each joint face for holding securely therebetween, together with the raised dimple segments, a pH-type acid paper having a sheet-like substrate along a flow of gaseous refrigerant through the member such that the gaseous refrigerant flows over an outer surface of the substrate, wherein the raised dimple segments, in an assembled state, constitute a dimple configured to open a Schrader-valve when the kit is temporarily held against the valve for permitting a flow of gaseous refrigerant therethrough to the atmosphere.

17. A method for testing for presence of acid in refrigerant of a refrigeration system or a recovered refrigerant vessel, comprising the steps of removably inserting a holder fixture with pH-type acid paper having a sheet-like substrate held by the holder fixture in a transparent member open at both ends such that the substrate is disposed along a flow of gaseous refrigerant through the member such that the gaseous refrigerant flows over an outer surface of the substrate;

placing the transparent member against a service valve at one of the refrigeration system and the recovered refrigerant vessel to open the service valve for permitting gaseous refrigerant to flow therethrough; and holding the transparent member against the service valve for a predetermined period as vapor refrigerant flows therethrough to the atmosphere and observing a color change in the paper.

18. A hollow transparent tube open at upstream and downstream ends thereof and internally configured to removably and securely hold therein acid indicator assembly for a refrigerant vapor test kit, said acid indicator assembly having a holder fixture and a sheet-like substrate held by the holder fixture disposed along a flow of gaseous refrigerant through the tube, wherein the upstream end of the tube is configured to be held temporarily against a service valve at one of a compressor suction side inlet of a refrigeration system and a recovered refrigerant vessel for permitting the flow of gaseous refrigerant through the tube and over an outer surface of the substrate into the atmosphere.

19. An acid indicator assembly for a test kit, comprising a tapered holder fixture having two panels arranged to be folded together, and a pH-type acid indicator paper held between the panels and having a sheet-like substrate disposed along a flow of gaseous refrigerant through the fixture, said fixture being sized to provide a tight friction fit with a viewing member open at both ends and configured to be held temporarily against a service valve at one of a refrigeration system and a recovered refrigerant vessel for permitting the flow of gaseous refrigerant through the fixture and over an outer surface of the substrate into the atmosphere.

20. The assembly according to claim 19, wherein the fixture defines a dimple between the panels at one side of the member, the dimple being configured to open the service valve constituted by a Schrader-valve.

21. The assembly according to claim 19, wherein the panels have a color matching a color of the indicator paper in an unreacted state.

22. The assembly according to claim 19, wherein the panels have a color matching a color of the indicator paper in an reacted state.

23. The assembly according to claim 19, wherein each of the panels has an aperture to expose the indicator paper held therebetween to the gaseous refrigerant flow from the service valve.

24. The assembly according to claim 23, wherein the dimple constitutes a bridging portion joining the panels.

25. An acid indicator assembly for a test kit, comprising a flat rigid holder, and pH-type indicator paper having a sheet-like substrate disposed along a flow of gaseous refrigerant along the holder extending along one side of the holder over an upstream face of the holder and along another side of the holder, said rigid holder being sized to provide a tight friction fit in a viewing member open at both ends and configured to be held temporarily against a service valve at one of a refrigeration system and a recovered refrigerant vessel for permitting the flow of gaseous refrigerant along the holder and over an outer surface of the substrate into the atmosphere.

26. The assembly according to claim 25, wherein the holder has a dimple at one face, and the paper has an aperture through which the dimple extends to open the service valve constituted by a Schrader-valve.

27. An acid indicator assembly comprising a cylindrical piece sized and configured to extend transversely of a viewing member open at both ends, and pH-type acid paper having a sheet-like substrate disposed along a flow of gaseous refrigerant through the cylindrical piece arranged to extend around the piece in a downstream direction of the viewing member which is configured to be held temporarily against a service valve at one of a refrigeration system and a recovered refrigerant vessel for permitting the flow of gaseous refrigerant through the cylindrical piece and over an outer surface of the substrate into the atmosphere.

28. An acid indicator assembly, comprising a cylindrical piece sized and configured to extend transversely of a viewing member open at both ends, and a pH-type acid paper having a sheet-like substrate disposed along a flow of gaseous refrigerant through the cylindrical piece with an aperture through which the piece is arranged to extend a downstream direction of the viewing member which is configured to be held temporarily against a service valve at one of a refrigeration system and a recovered refrigerant vessel for permitting the flow of gaseous refrigerant through the cylindrical piece and over an outer surface of the substrate into the atmosphere.

* * * * *